US009400262B2

(12) United States Patent
Doller et al.

(10) Patent No.: US 9,400,262 B2
(45) Date of Patent: Jul. 26, 2016

(54) TESTING FOR DEFECTIVE MANUFACTURING OF MICROPHONES AND ULTRALOW PRESSURE SENSORS

(71) Applicant: Robert Bosch GmbH, Stuttgart (DE)

(72) Inventors: Andrew J. Doller, Sharpsburg, PA (US); Michael J. Daley, Santa Clara, CA (US)

(73) Assignee: Robert Bosch GmbH, Stuttgart (DE)

( * ) Notice: Subject to any disclaimer, the term of this patent is extended or adjusted under 35 U.S.C. 154(b) by 317 days.

(21) Appl. No.: 14/025,438

(22) Filed: Sep. 12, 2013

(65) Prior Publication Data

US 2014/0076052 A1    Mar. 20, 2014

Related U.S. Application Data

(60) Provisional application No. 61/701,001, filed on Sep. 14, 2012.

(51) Int. Cl.
*G01N 29/14* (2006.01)
*B81C 99/00* (2010.01)
*H04R 29/00* (2006.01)

(52) U.S. Cl.
CPC .............. *G01N 29/14* (2013.01); *B81C 99/005* (2013.01); *B81C 99/0045* (2013.01); *H04R 29/004* (2013.01); *H04R 2201/003* (2013.01)

(58) Field of Classification Search
CPC ............... B81B 2201/0257; B81B 2201/0264; H04R 19/005; H04R 29/004; H04R 19/04; G01N 29/14
USPC .......................................................... 73/587
See application file for complete search history.

(56) References Cited

U.S. PATENT DOCUMENTS

| 3,876,035 | A | * | 4/1975 | Eckel | G01H 3/00 181/198 |
|---|---|---|---|---|---|
| 4,065,647 | A | * | 12/1977 | Frye | G01H 3/00 381/60 |
| 5,029,215 | A | * | 7/1991 | Miller, II | H04R 1/38 367/13 |
| 5,433,104 | A | | 7/1995 | Kunze et al. | |

(Continued)

FOREIGN PATENT DOCUMENTS

| CN | 102186134 | 9/2011 |
|---|---|---|
| EP | 0813350 | 12/1997 |

(Continued)

OTHER PUBLICATIONS

International Search Report and Written Opinion for Application No. PCT/US2013/059476 dated Nov. 28, 2013 (11 pages).

*Primary Examiner* — Freddie Kirkland, III
(74) *Attorney, Agent, or Firm* — Michael Best & Friedrich LLP

(57) ABSTRACT

A method of testing a MEMS pressure sensor device such as, for example, a MEMS microphone package. The MEMS pressure sensor device includes a pressure sensor positioned within a housing and a pressure input port to direct acoustic pressure from outside the housing towards the pressure sensor. An acoustic pressure source is activated and acoustic pressure from the acoustic pressure source is directed to the pressure input port and to an exterior location of the housing other than the pressure input port. Based on the output signal of the pressure sensor, it is determined whether any defects exist that allow acoustic pressure to reach the pressure sensor through the exterior of the housing at locations other than the pressure input port.

16 Claims, 5 Drawing Sheets

(56) References Cited

U.S. PATENT DOCUMENTS

| | | | |
|---|---|---|---|
| 5,463,893 A * | 11/1995 | Pla | H04R 3/002 702/190 |
| 8,036,401 B2 * | 10/2011 | Poulsen | H04R 19/005 381/111 |
| 8,336,670 B2 * | 12/2012 | Viehmann | H04R 29/004 181/198 |
| 8,848,931 B2 * | 9/2014 | Schaule | H04R 29/004 381/58 |
| 2005/0013444 A1 | 1/2005 | Dorfman et al. | |
| 2007/0019815 A1 | 1/2007 | Asada et al. | |
| 2007/0205492 A1 * | 9/2007 | Wang | B81C 1/0023 257/659 |
| 2007/0269051 A1 * | 11/2007 | Weidner | G10K 11/1788 381/60 |
| 2009/0129612 A1 * | 5/2009 | Takeuchi | H01G 7/025 381/174 |
| 2009/0296946 A1 | 12/2009 | Zhang | |
| 2010/0074451 A1 | 3/2010 | Usher et al. | |
| 2010/0135501 A1 | 6/2010 | Corbett et al. | |
| 2010/0246855 A1 | 9/2010 | Chen | |
| 2010/0290634 A1 * | 11/2010 | Schaule | H04R 29/004 381/58 |
| 2014/0328489 A1 * | 11/2014 | Ziegler | H04R 29/004 381/58 |
| 2015/0010157 A1 * | 1/2015 | Doller | H04R 29/004 381/58 |

FOREIGN PATENT DOCUMENTS

| | | |
|---|---|---|
| WO | 2010026724 | 3/2010 |
| WO | 2012004339 | 1/2012 |
| WO | 2013001316 | 1/2013 |

* cited by examiner

TESTING FOR DEFECTIVE MANUFACTURING OF MICROPHONES AND ULTRALOW PRESSURE SENSORS

RELATED APPLICATIONS

This application claims the benefit of U.S. Provisional Patent Application No. 61/701,001, filed on Sep. 14, 2012 and entitled "TESTING FOR DEFECTIVE MANUFACTURING OF MICROPHONES AND ULTRALOW PRESSURE SENSORS," the entire contents of which are incorporated herein by reference.

BACKGROUND

The present invention is used to detect manufacturing defects of an assembled microphone or an ultra-low pressure transducer.

SUMMARY

In one embodiment, the invention provides a method of testing a MEMS pressure sensor device such as, for example, a MEMS microphone package. The MEMS pressure sensor device includes a pressure sensor positioned within a housing and a pressure input port to direct acoustic pressure from outside the housing towards the pressure sensor. An acoustic pressure source is activated and acoustic pressure from the acoustic pressure source is directed to the pressure input port and to an exterior location of the housing other than the pressure input port. Based on the output signal of the pressure sensor, it is determined whether any defects exist that allow acoustic pressure to reach the pressure sensor through the exterior of the housing at locations other than the pressure input port.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
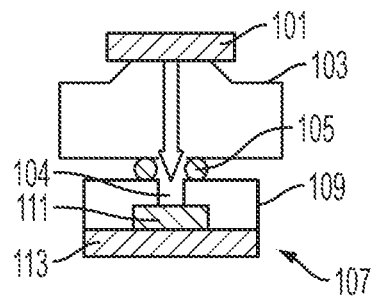
FIG. 1 is a schematic view of a testing arrangement applied to a properly manufactured microphone.

FIG. 1 illustrates a first example of a testing arrangement for testing the output of a MEMS pressure sensor device 107, referred to as a device under test (DUT). A speaker 101 is located at one end of a chamber 103, and the speaker 101 is positioned to emit test sounds into the chamber 103. A straight arrow indicates an acoustic path from the speaker 101 to the pressure input port 104 of a DUT 107. A gasket 105 is positioned between the chamber 103 and a lid 109 of the DUT 107 such that the acoustic path is defined and acoustically isolated. In other constructions, a seal is formed between the chamber and the lid 109 without the use of a gasket. The DUT 107 includes a base 113. In some constructions, the base is formed of a silicon substrate and may include one or more circuit components. In the example of FIG. 1, the base 113 is a substrate with a transducer 111 located thereon. A lid 109 is attached to the base 113 to form a housing which encloses the transducer 111. The lid 109 protects the transducer 111 and prevents sound from entering the housing at locations other than the pressure input port 104 and affecting the operation of the transducer 111. The testing arrangement of FIG. 1 is intended primarily to test the performance of the transducer 111. It does not provide for evaluation of the housing or the quality of the seam where the lid 109 is attached to the base 113.

Figure 2:
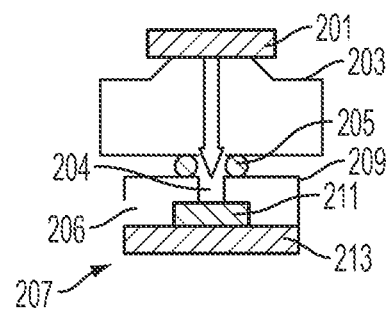
FIG. 2 is a schematic view of the testing arrangement in FIG. 1 applied to a defective microphone.

FIG. 2 illustrates a limitation of the testing arrangement in FIG. 1 when testing a MEMS pressure sensor device that has a manufacturing defect in the lid. The testing arrangement depicted in FIG. 2 has the same configuration as the testing arrangement illustrated in FIG. 1. A speaker 201 is located at one end of a chamber 203, and the speaker 201 is positioned to emit test sounds into the chamber 203. A straight arrow indicates an acoustic path from the speaker 201 to the pressure input port 204 of a DUT 207. A gasket 205 is positioned between the chamber 203 and a lid 209 of the DUT 207 such that the acoustic path is defined and acoustically isolated. The DUT 207 includes a base 213, a transducer 211 located on the base 213, and a lid 209 that is attached to the base 213 and enclosing the transducer 211.

In FIG. 1, the lid 109 is represented by a solid line indicating a properly manufactured device. In particular, the seam formed between the lid 109 and the base 113 is complete and does not allow acoustic pressure to enter the housing. However, in the example of FIG. 2, there is a break 206 between the lid 209 and the base 213. This break 206 represents a defect in the microphone housing such as, for example, a defected seal between the lid 209 and the base 213. Because the testing arrangement depicted in FIGS. 1 and 2 does not provide an acoustic source or an acoustic path for sound to enter the transducer 211 through potential holes in a defective housing, manufacturing defects such as these cannot be detected.

Figure 3:
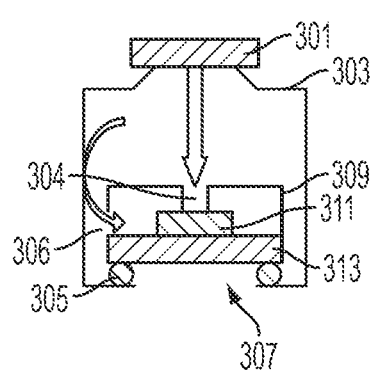
FIG. 3 is a schematic view of another testing arrangement according to one embodiment using one chamber and one acoustic source applied to a defective microphone.

FIG. 3 illustrates a schematic view of an alternative testing arrangement which, in addition to providing acoustic pressure to the pressure input port 304 of the DUT 307, also provides acoustic pressures to the exterior of the housing of the DUT 307. In this arrangement, the DUT 307 is positioned at least partially inside the testing chamber 303 so as to expose the entire exterior of the lid 309, including the seam between the lid 309 and the base 313, to the test sound. A speaker 301 is located at one end of a chamber 303, and the speaker 301 is positioned to emit test sounds into the chamber 303. A straight arrow indicates an acoustic path from the speaker 301 to the pressure input port 304 of a DUT 307. A gasket 305 is positioned between the chamber 303 and a lid 309 of the DUT 307 such that the acoustic path is defined and acoustically isolated. Sound from the speaker 301, as represented by the straight arrow, enters the pressure input port 304 to reach the transducer 311. Furthermore, if a defective microphone housing includes any other openings, such as, for example, break 306, the sound from the speaker 301 also enters the housing through the break 306 as represented by the curved arrow and affects the operation of the transducer 311.

Figure 4:
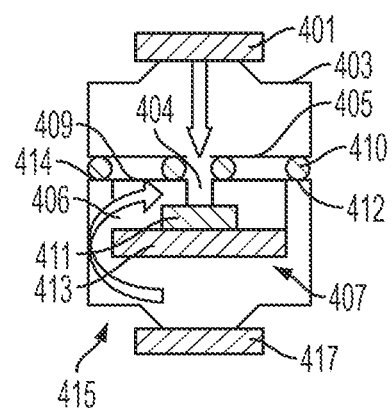
FIG. 4 is a schematic view of a testing arrangement according to another embodiment using two chambers and two acoustic sources applied to a defective microphone.

FIG. 4 illustrates another example of a testing arrangement that is able to detect manufacturing defects in the housing by exposing the exterior of the housing to acoustic pressure. A first speaker 401 is located at one end of a first chamber 403, and the speaker 401 is positioned to emit test sounds into the first chamber 403. A gasket 405 is positioned between the first chamber 403 and a lid 409 of the DUT 407 such that an acoustic path is defined and acoustically isolated. In this example, a second chamber 415 aligns with the first chamber 403, and encloses the DUT 407. A surface 410 of the second chamber 415 presses against a surface 412 of the first chamber 403 such that a seal is formed between the surfaces. In the construction illustrated in FIG. 4, the seal between the surfaces of the two chambers is formed by a gasket 414. However, as noted above, in other constructions, the seal between various components can be formed without the use of a gasket 414. The seal acoustically isolates the interiors of each chamber from the exterior and from each other.

As in the other figures, the DUT 407 includes a base 413, a transducer 411 located on the base 413, and a lid 409 that is attached to the base 413 to enclose the transducer 411. The lid 409 protects the transducer 411 and prevents sound from entering the transducer 411 at locations other than the pressure input port 404. The testing arrangement of FIG. 4 also includes a second speaker 417 located at one end of the second chamber 415 that is positioned to emit sound into the second chamber 415.

Sounds emitted from the first speaker 401 pass through the pressure input port 404 and are detected by the transducer 411. As described in detail below, in a properly constructed microphone package, the sounds from the first speaker 401 will produce a defined frequency response profile. However, when breaks 406 or leaks are present in a defective microphone package, sounds from the second speaker 417 (as represented by the curved arrow) can pass through holes in the lid 409 and can alter the frequency response profile detected by the transducer 411. The sound from the second speaker 417 as well as the size and shape of the testing chamber 415 are controlled so that the sound from the second speaker 417 can be distinguished from the sound from the first speaker 401.

Figure 5:
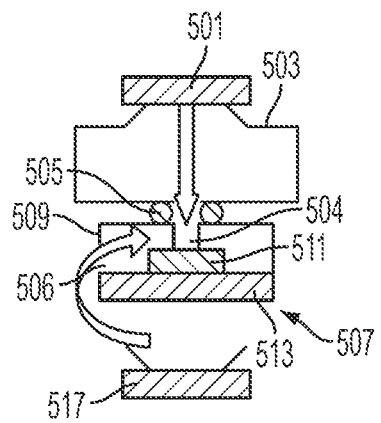
FIG. 5 is a schematic view of a testing arrangement according to yet another embodiment using one chamber and two acoustic sources applied to a defective microphone.

FIG. 5 illustrates yet another example of a testing arrangement. Again, a speaker 501 is located at one end of a first chamber 503, and the speaker 501 is positioned to emit test sounds into the chamber 503. The straight arrow indicates an acoustic path from the speaker 501 to the pressure input port 504 of a DUT 507. A gasket 505 is positioned to form a seal between the chamber and the lid 509 of the DUT 507 such that an acoustic path is defined and acoustically isolated. As in the other figures, the DUT 507 includes a base 513, a transducer 511 located on the base 513, and a lid 509 that is attached to the base 513 to enclose the transducer 511. The lid 509 protects the transducer 511 and restricts sound from entering the transducer 511 at locations other than the pressure input port 504. The example of FIG. 5 includes a second speaker 517 that is mounted on the side of the DUT 507 opposite the chamber 503 and applies sound around the exterior of the housing of the DUT 507. Sounds from this second speaker 517 can pass through breaks 506 in a defective DUT housing (as illustrated by the curved arrow) and affect the frequency response profile of the transducer 511.

Figure 6:
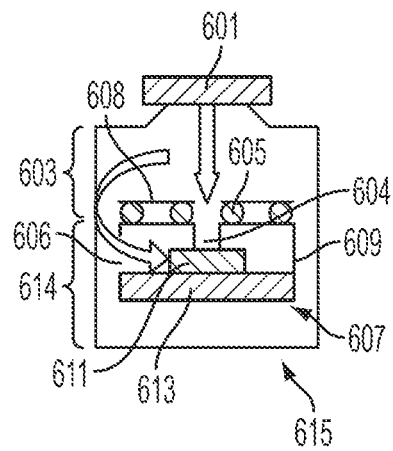
FIG. 6 is a schematic view of a testing arrangement according to still another embodiment using two sections that form one testing chamber and one speaker applied to a defective microphone.

FIG. 6 illustrates another example of a testing arrangement. A speaker 601 is located at one end of a first chamber 603, and the speaker 601 is positioned to emit test sounds into the chamber 603. As indicated by the straight arrow, sound follows an acoustic path from the speaker 601 to the pressure input port 604 of a DUT 607. A gasket 605 is positioned between the chamber 603 and the lid 609 of the DUT 607 such that an acoustic path is defined and the pressure input port 604 is acoustically isolated. The DUT 607 again includes a base 613, a transducer 611 located on the base 613, and a lid 609 that is attached to the base 613 to enclose the transducer 611. The lid 609 protects the transducer 611 and restricts sound from entering the transducer 611 at locations other than the pressure input port 604.

The DUT 607 is positioned on a surface 608 within the chamber 615. A gasket 605 supports the DUT 607 and isolates the acoustic pathway from the speaker 601 as illustrated by the straight line. In the example of FIG. 6, a complete testing chamber 615 includes two separate sections, a first chamber section 603 and a second chamber section 614, that align and enclose the DUT 607 when the DUT 607 is positioned on the testing surface 608. The complete testing chamber 615 defines and controls the acoustic paths so that the acoustic paths are uniform from test to test. In addition to directing sound from the speaker 601 to the pressure input port 604, the testing chamber 615 exposes the base 613 and the lid 609 of the DUT 607 to sound from the speaker 601. As such, the sound from the speaker 601 can pass through any breaks 606 or leaks in a defective DUT 607 and can affect the frequency response profile of the transducer 611.

Figure 7:
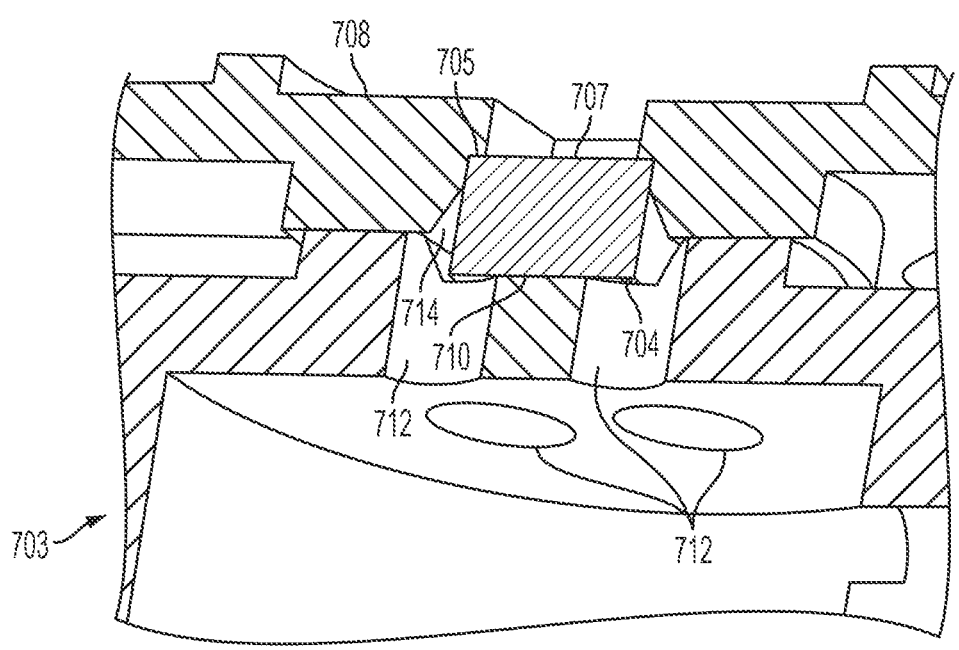
FIG. 7 is a cross-sectional view of the testing arrangement of FIG. 6.

The cross-sectional view of FIG. 7 further illustrates the testing arrangement of FIG. 6 for a different type of DUT 707. In this example, the pressure input port 704 is located in a corner of the DUT housing instead of being located at the center of the lid. The DUT 707 is positioned against a surface 705 of a holder 708. A seal is formed between the surface 705 and the DUT 707. A surface 710 of a chamber 703 presses against the housing of the DUT 707, and thus, presses the DUT 707 against the surface 705 of the holder 708. This forms an antechamber 714 around the DUT 707. Sound ports 712 in the chamber 703 are located proximal to the DUT 707. One sound port 712 provides an acoustic path from the chamber 703 to the pressure input port 704 of the DUT 707. Additional sound ports provide for acoustic paths from the chamber 703 to the antechamber 714. This acoustic path allows sound to surround the lid 709 of the DUT 707. If there are any leaks in the housing of the DUT 707, then this sound can affect the frequency response profile of the transducer 711.

Figure 8:
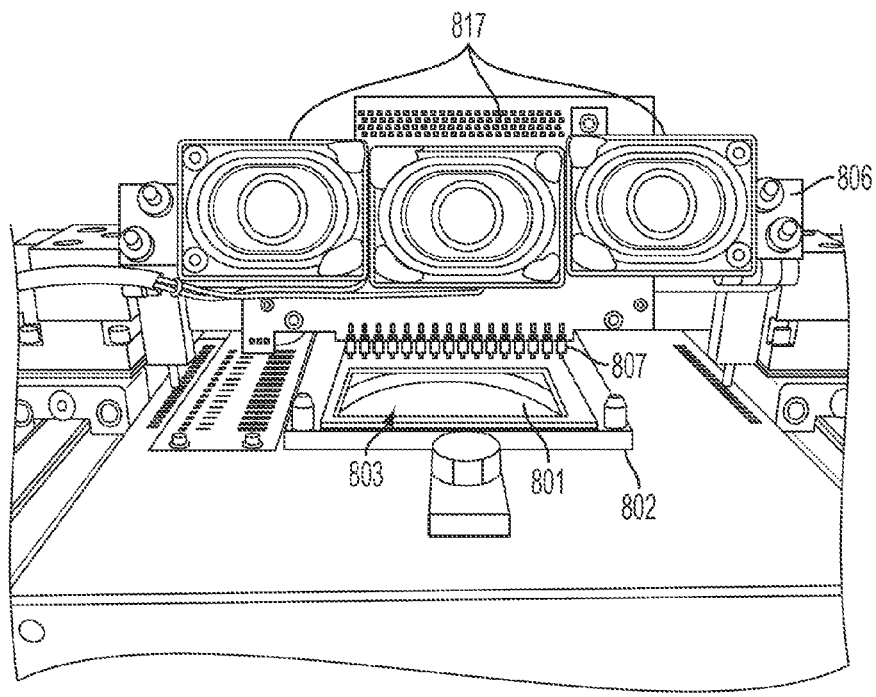
FIG. 8 is a perspective view of the testing arrangement of FIG. 5 with a speaker array serving as a second sound source in a raised and inactive position.

The picture in FIG. 8. is an implementation of testing arrangement based on the schematic example illustrated in FIG. 5 and is configured for testing multiple MEMS sensor devices simultaneously. The first speaker 801 is positioned under the DUT holder 802. The DUT holder 802 covers the speaker 801, and forms the chamber 803. The DUT holder 802 supports either a single DUT 807 or an array of DUTs 807 during testing. The DUT holder 802 forms a seal with the array of DUTs 807. However, unlike the example of FIG. 5, the DUT holder 802 in FIG. 8 does not utilize a gasket 505 to form a seal between the chamber 803 and the array of DUTs 807. Instead, the DUT holder 802 uses a pressure fit to form a seal during testing.

Figure 9:
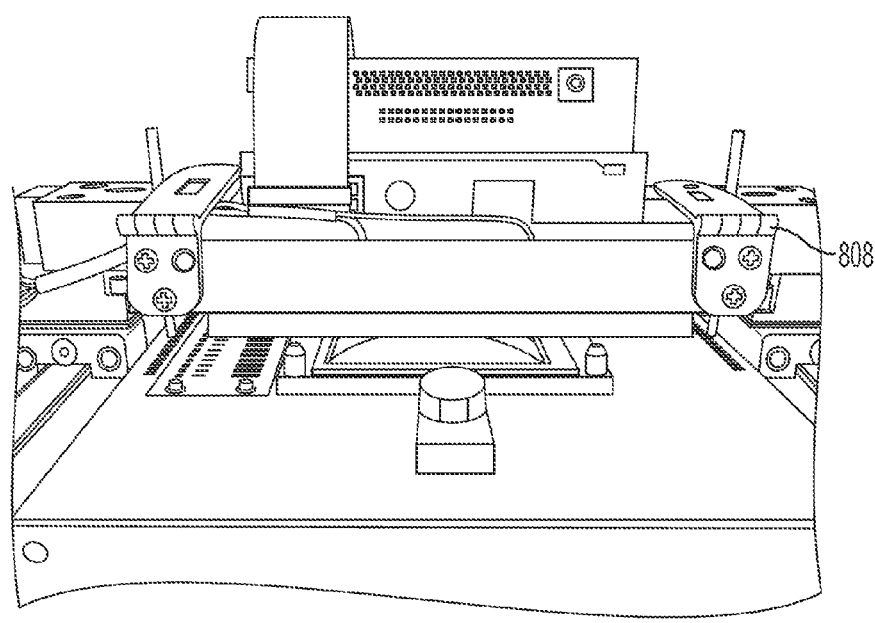
FIG. 9 is a perspective view of the testing arrangement depicted in FIG. 5 with the speaker array in a lowered and active position.

An array of speakers 817 is positioned on an armature 806 that extends above the DUT holder 802. As illustrated in FIG. 9, the armature 806 is connected to a hinge 808 that allows the array of speakers 817 to pivot so that the array of speakers 817 faces the DUTs 807 during testing. The array of speakers 817 are shown in FIG. 8. in the inactive upper position. In FIG. 9, the array of speakers 817 is shown in the lower active position.

Figure 10:
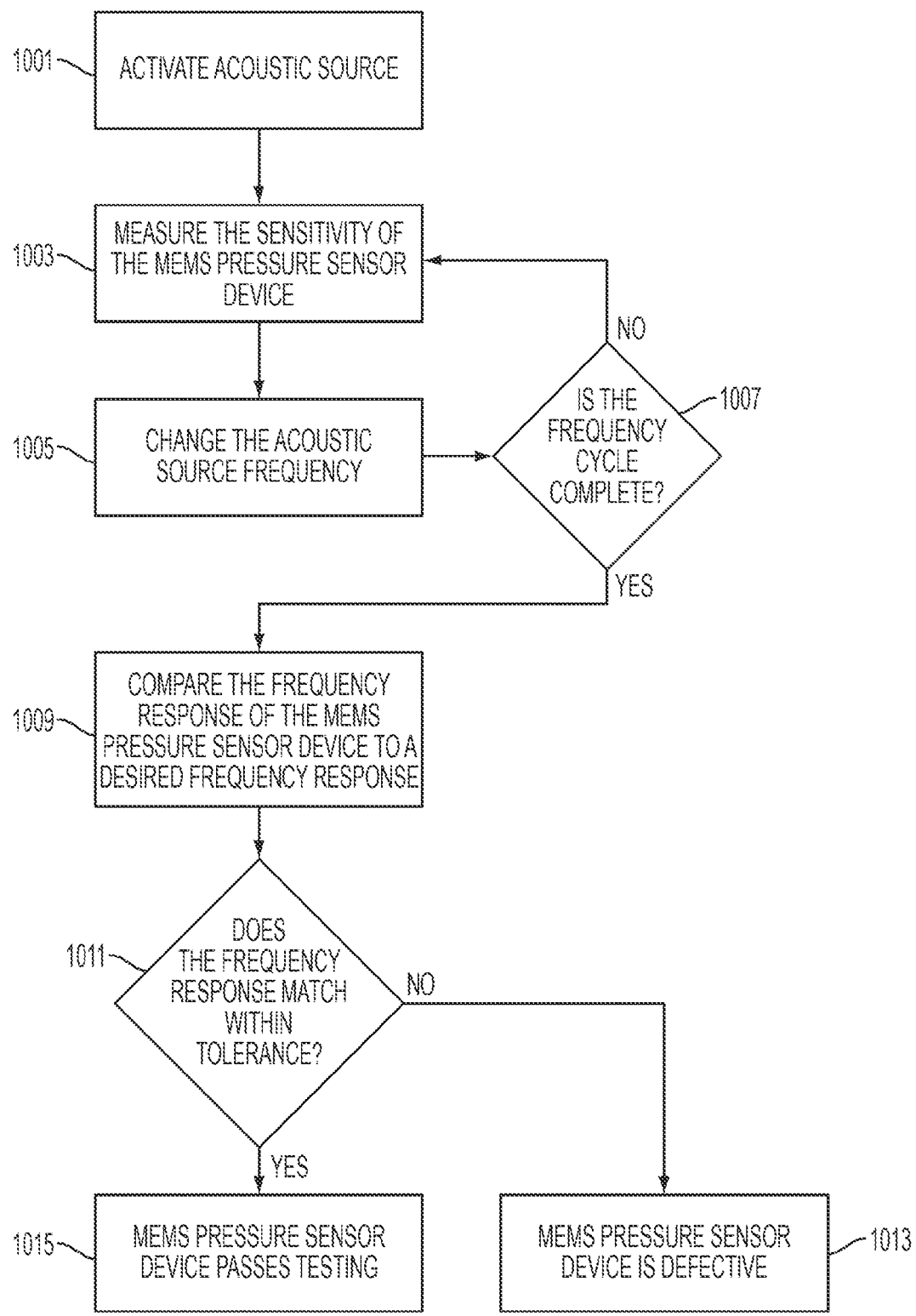
FIG. 10 is a flowchart illustrating a testing process using at least one of the testing arrangements of FIGS. 3-6.

The flowchart of FIG. 10 demonstrates a process for testing a microphone for manufacturing defects using any one of the testing arrangements illustrated in FIGS. 3-9. Once the DUT is positioned within the testing arrangement, one or more speakers are activated to produce a test sound (step 1001). The sensitivity of the MEMS pressure sensor device is measured (step 1003) as the speaker is cycled through a range of audio frequencies (step 1005). When the cycle is complete (step 1007), the measured frequency response profile is compared to a desired frequency response profile (step 1009). If the difference between the measured frequency response profile of the DUT and the desired frequency response profile is outside the desired sensitivity range at any frequency (step 1011), the DUT will be identified as defective (step 1013). However, if the difference between the measured and desired frequency response profiles is within a defined tolerance (step 1011), then the construction of the DUT housing is verified and the DUT passes the test (step 1015).

Figure 11:
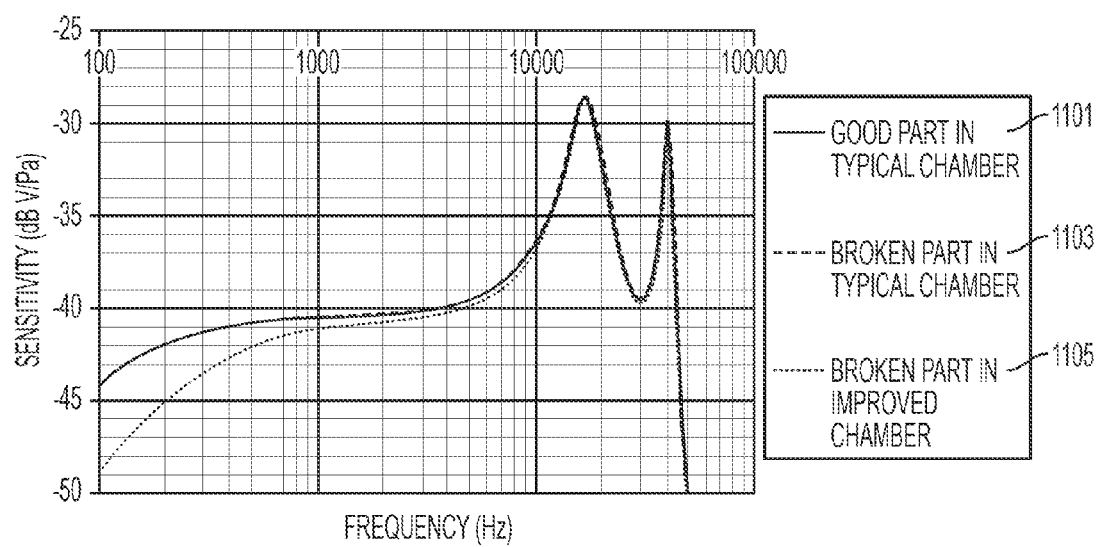
FIG. 11 is a graph of microphone sensitivity over a range of audio frequencies illustrating an output test of the testing arrangements of FIGS. 1, 2, and 5 using the testing process of FIG. 10.

FIG. 11 illustrates examples of frequency response profiles that are measured using the method of FIG. 10. Profile 1101 represents the measured frequency response profile of a properly constructed DUT over a frequency range. Profile 1103 represents the frequency response profile of a defective DUT using the testing arrangement of FIGS. 1 and 2. As described above, the testing arrangements of FIGS. 1 and 2 do not expose the exterior of the DUT housing to sound. Therefore, profiles 1101 and 1103 are identical despite the manufacturing defect in the lids of the DUTs.

In contrast, profile 1105 represents the frequency response profile of a defective DUT using one of the testing arrangements illustrated in FIGS. 2-9. Profile 1105 illustrates a decrease in sensitivity at low frequencies that is caused by leakage of sound through the lid of the defective DUT. This difference in sensitivity between properly constructed and defective DUTs allows for the identification of manufacturing defects that is not possible with testing arrangements that isolate and direct sound only into the pressure input port of the DUT.

Thus, the invention provides, among other things, a testing arrangement that allows for a method of detecting manufacturing defects in the lids of MEMS pressure sensors. Various features and advantages of the invention are set forth in the following claims.

What is claimed is:

1. A method of testing a MEMS pressure sensor device, the MEMS pressure sensor device including a pressure sensor positioned within a housing and a pressure input port to direct acoustic pressure from outside the housing toward the pressure sensor, the method comprising:
   activating an acoustic pressure source;
   directing acoustic pressure from the acoustic pressure source to the pressure input port;
   directing acoustic pressure from the acoustic pressure source to an exterior location of the housing other than the pressure input port; and
   determining, based on an output signal of the pressure sensor, whether any defects exist that allow acoustic pressure to reach the pressure sensor through the exterior of the housing at locations other than the pressure input port.

2. The method of claim 1, further comprising the acts of:
   positioning the MEMS pressure sensor device proximal to a first testing chamber, wherein the first testing chamber includes a pressure output port, wherein a first speaker of the acoustic pressure source produces acoustic pressure within the first testing chamber, and wherein the acoustic pressure produced by the first speaker exits the first testing chamber through the pressure output port; and
   aligning the pressure input port of the MEMS pressure sensor device with the pressure output port of the first testing chamber, wherein the act of directing acoustic pressure from the acoustic pressure source to the pressure input port includes directing acoustic pressure from the first testing chamber through the pressure output port of the first testing chamber and into the pressure input port of the MEMS pressure sensor device.

3. The method of claim 2, wherein the act of directing acoustic pressure from the acoustic pressure source to an exterior location of the housing other than the pressure input port includes positioning a second speaker of the acoustic pressure source proximal to the MEMS pressure sensor device such that the output of the second speaker is directed toward a surface of the MEMS pressure sensor device housing other than the pressure input port.

4. The method of claim 3, further comprising the act of forming a seal between the pressure input port of the MEMS pressure sensor device and the pressure output port of the first testing chamber such that the pressure input port is acoustically isolated from the output of the second speaker.

5. The method of claim 4, wherein the act of forming a seal includes positioning a gasket between the MEMS pressure sensor device and the first testing chamber.

6. The method of claim 2, further comprising the act of wherein the act of directing acoustic pressure from the acoustic pressure source to the exterior location of the housing other than the pressure input port includes activating a second speaker of the acoustic pressure source to produce acoustic pressure within a second testing chamber, and
   further comprising the act of positioning the MEMS pressure sensor device proximal to the second testing chamber such that at least a portion of the housing, other than the pressure input port, is positioned within the second testing chamber and is exposed to the acoustic pressure from the second speaker.

7. The method of claim 6, further comprising the acts of:
   forming a first seal between the pressure input port of the MEMS pressure sensor device and the pressure output port of the first testing chamber such that the pressure input port is acoustically isolated from the output of the second speaker; and
   forming a second seal between the first testing chamber and the second testing chamber such that the interior of the first testing chamber and the interior of the second testing chamber are acoustically isolated from external sound.

8. The method of claim 7, wherein the act of forming the first seal includes positioning a gasket between the MEMS pressure sensor device and the first testing chamber, and wherein the act of forming the second seal includes positioning a gasket between the first testing chamber and the second testing chamber.

9. The method of claim 1, further comprising the act of positioning the MEMS pressure sensor device inside of a testing chamber,
   wherein the act of directing acoustic pressure from the acoustic pressure source to the pressure input port includes activating a speaker of the acoustic pressure source to generate acoustic pressure within the testing chamber, wherein acoustic pressures generated within the testing chamber enter the pressure input port, and
   wherein the act of directing acoustic pressure from the acoustic pressure source to the exterior location of the housing other than the pressure input port includes the act of activating the speaker to generate acoustic pressure within the testing chamber, wherein the exterior location of the housing other than the pressure input port is exposed to the acoustic pressures generated within the testing chamber.

10. The method of claim 9, wherein, when the MEMS pressure sensor device is positioned inside the testing chamber, a surface opposite the pressure input port forms a seal with the testing chamber such that the inside of the testing chamber is acoustically isolated from external sounds.

11. The method of claim 10, wherein the act of forming the seal includes positioning a gasket between the testing chamber and the surface opposite to the pressure input port.

12. The method of claim 9, wherein the act of positioning the MEMS pressure sensor device inside of a testing chamber further comprises the act of positioning the MEMS pressure sensor device on a surface within the testing chamber, wherein the testing chamber includes a top half chamber and a bottom half chamber, wherein the top half chamber aligns with the bottom half chamber such that a seal is formed between the two half components.

13. The method of claim 12, wherein the act of positioning the MEMS pressure sensor device inside of the testing chamber includes placing one or more gaskets between the MEMS pressure sensor device and the surface within the testing chamber such that a seal is formed, the seal isolating an acoustic path to the pressure input port from an acoustic path to the exterior location of the housing other than the pressure input port.

14. The method of claim 13, wherein the act of positioning the MEMS pressure sensor device inside of the testing chamber includes closing the two half components around the MEMS pressure sensor device such that an antechamber forms around the housing of the MEMS pressure sensor device, wherein a controlled amount of acoustic pressure from the speaker is directed into the antechamber such that the housing of the MEMS pressure sensor device is exposed to acoustic pressure.

15. The method of claim 1, wherein the act of analyzing the output signal of the pressure sensor further comprises the acts of:
   receiving the output signal from the pressure sensor;
   comparing the frequency response of the output signal with a desired frequency response; and
   determining that the MEMS pressure sensor device is defective when the difference in the output signal and a desired output signal exceeds a threshold.

16. The method of claim 1, wherein the MEMS pressure sensor device includes a MEMS microphone package.

* * * * *